US00PP08564P

United States Patent [19]

Button

[11] Patent Number: Plant 8,564

[45] Date of Patent: Jan. 25, 1994

[54] ANTHURIUM PLANT NAMED PATTI-ANNE

[76] Inventor: Richard J. Button, 1245 Obispo Ave., Coral Gables, Fla. 33134

[21] Appl. No.: 872,039

[22] Filed: Apr. 22, 1992

[51] Int. Cl.[5] ..... A01H 5/00
[52] U.S. Cl. ..... Plt./88.1
[58] Field of Search ..... Plt. 88.1

*Primary Examiner*—James R. Feyrer
*Assistant Examiner*—Erich Veitenheimer
*Attorney, Agent, or Firm*—Foley & Lardner

[57] ABSTRACT

An Anthurium plant named Patti-Anne characterized by its tall growth habit, large and wide leaves, and its purple spathe and spadix.

1 Drawing Sheet

The invention relates to a new and distinct cultivar of Anthurium plant, botanically known as *Anthurium antigua*, and known by the cultivar name Patti-Anne.

The new cultivar is a product of a planned breeding program carried out by the inventor, Richard J. Button, in Coral Gables, Fla. The cross resulting in the new cultivar was between parents which are unknown at this time. The new cultivar was discovered and selected while growing among the progeny of the cross by the inventor. Propagation by division was used to increase the number of plants for evaluation, and the stability of the combination of characters from generation to generation was clearly demonstrated.

The following observations, measurements and values describe plants grown in Palmdale, Fla. under greenhouse conditions which closely approximate those generally used in horticultural practice.

The following traits have been repeatedly observed to be characteristics which in combination distinguish Patti-Anne from other Anthuriums of the *A. antigua* type.

1. Patti-Anne has a large purple flower of the traditional cordate type while other *A. antigua* types have a small purple flower that is a thin flag type.

2. Patti-Anne is much taller than other *A. antigua* cultivars and has larger, wider leaves.

3. The flowers of Patti-Anne have a spicy fragrance as do other *A. antigua* cultivars.

4. The combined characteristics of Patti-Anne produce a unique cultivar that cannot be meaningfully compared to other anthuriums of this type.

The accompanying color photograph illustrates in top perspective view the overall appearance of Patti-Anne, with the colors being as true as reasonably possible in color reproductions of this type.

All color references are measured against The Royal Horticultural Society Colour Chart. Colors are as closely approximate as possible since color, as well as other phenotypical characteristics, depends on horticultural practices such as light level, temperature and fertilization rate, among others, without, however, any variance in the genotype.

Origin: Seedling from unknown parents.

Classification: *A. antigua*, c.v. Patti-Anne.

Propagation: Asexual production either through tissue culture or division.

Plant: In a 10" pot, Patti-Anne will grow to the mature size of approximately 45 cm to 55 cm in height and approximately 70 cm to 90 cm in width under appropriate growing conditions from division.

Leaves:

*Form.*—The leaf blade is ovate having an acuminate tip and a trucate base. The margin is entire and moderately wavy along the edge. The midrib tends to curve down toward the base. The leaf blade is thick and tends to be straight over the entire width of the leaf. The leaf surface is shiny with a smooth appearance.

*Size.*—Leaf blades of a mature sized plant are approximately 20 cm to 25 cm in length and approximately 14 cm to 16 cm in width.

*Petiole.*—The petiole is approximately 28 cm to 31 cm in length from the base of the petiole to the base of the leaf blade on the primary shoot. Secondary shoots are somewhat smaller depending on the age of the shoot. The petiole is approximately 3 mm in diameter just below the geniculum. The petiole is straight.

*Petiole wings.*—Petiole wings are approximately 3 mm to 3.5 mm in length and approximately 4 mm to 6 mm in width at its midpoint. The tip of the petiole wings are acute. The distance between the top of the wings and the base of the leaf is approximately 25 cm to 29 cm.

*Geniculum.*—The geniculum is approximately 25 mm to 30 mm in length and approximately 4 mm to 6 mm in diameter. The color is closest to 146A but with reddish tint due to presence of anthocyanin. The geniculum is curved and prominent. There is no space between the top of the geniculum and the base of the leaf blade.

*Veins.*—Veins are sunken with the leaf blade flat between veins on the top side. Veins are protruding on the underside. There are approximately 7 primary veins on the leaf.

*Color.*—Mature leaf: Upper side: Greener than 147A. Under side: Closest to 138B, but actual color is somewhat darker and greyer. Upper side midrib: Greener than 152B. Under side midrib: 150C. Petiole: Redder than 146A. Petiole wing: Lighter than 145A.

Inflorescence:

*Immature.*—The spathe is tightly rolled around the spadix and extrudes from the petiole sheath. The spathe is fully open approximately when the pedicel is fully elongated — approximately 30 cm to 50 cm in length.

*Mature.*—Spathe: Size: The flattened spathe is approximately 10 cm to 11.5 cm high and approximately 7.0 cm to 8.0 cm in width: Color: Fully open: Front: 186C. Back: 186D. Faded: Front: Lighter than 49D. Back: Closest to 155D, but slightly infused with red. Arrangement: The spathe stands up on straight wiry pedicels and opens vertically above the leaves. Shape: The spathe is cordate with an aristate apice that is twisted. The base is cordate. The spathe is reflexed when first opened and is approximately 9 cm to 11 cm in height and approximately 7.5 cm to 8.5 cm in width. It is approximately 7 mm to 12 mm in depth. Flowering time: After approximately 40 weeks for an untreated plant depending on season, approximately 1 to 3 blossoms will be present. Smaller blossoms may occur on less mature growth.

Reproductive organs:

*Spadix.*—Size: Approximately 5 cm to 6 cm in height and approximately 7.5 mm to 8.5 mm in width. Color: When the spathe unrolls, the spadix is darker than 186C gradually changing to lighter than 185D before senescing. Stamens: Anthers and filaments are not clearly visible. Pollen: White in color. Pistil: Lighter than 186C in color, protruding between the staminate flowers, firmly fixed to the main axle. The pistilate flowers extend approximately 2 mm beyond the staminate flowers.

*Roots.*—Fleshy.

General observations: Patti-Anne is a unique new Anthurium cultivar. It is larger in all respects than other Anthurium cultivars of this type and has a novel purple spathe and spadix.

I claim:

1. A new cultivar and distinct cultivar of Anthurium plant named Patti-Anne, as illustrated and described.

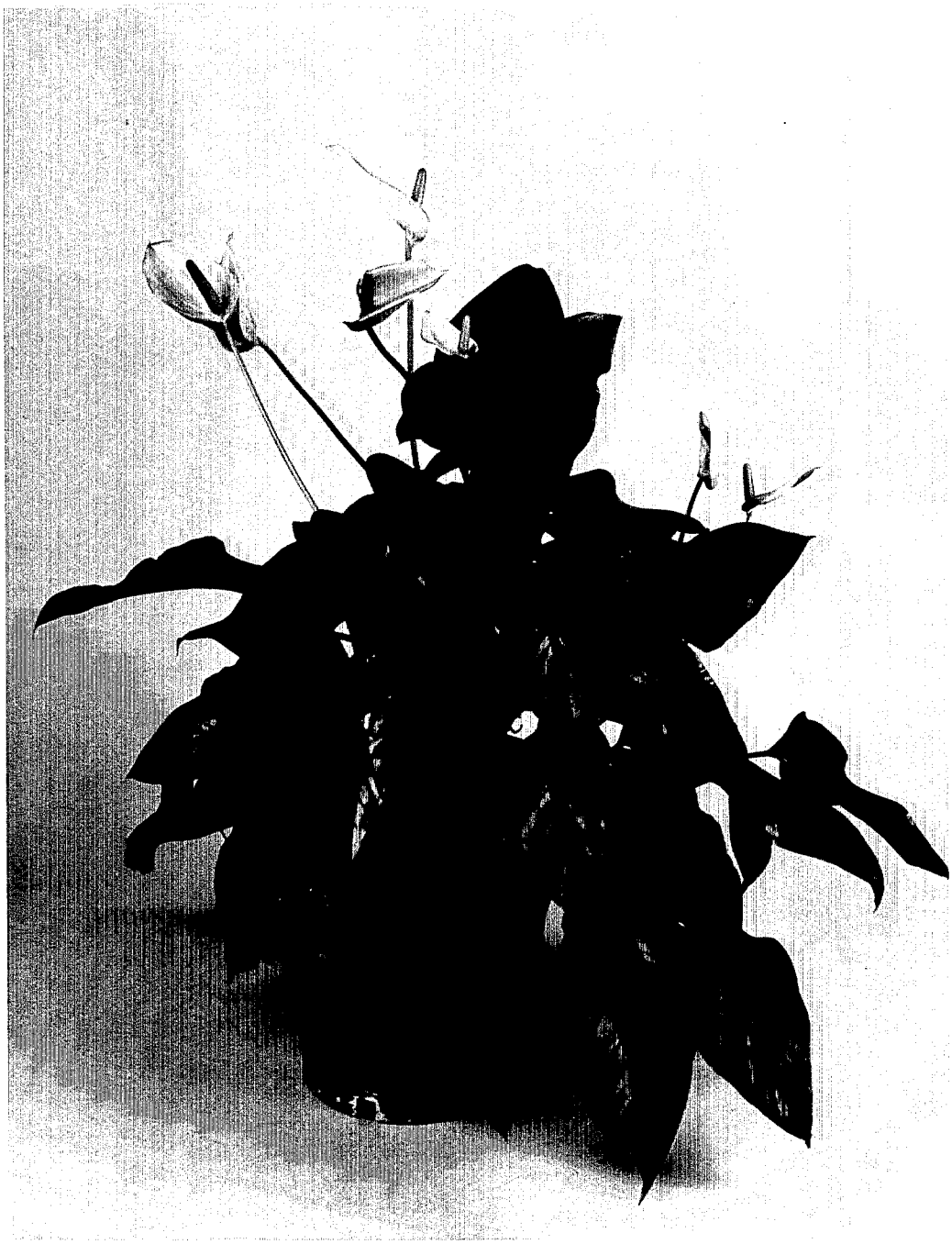

* * * * *